United States Patent [19]
Snyder et al.

[11] Patent Number: 5,470,479
[45] Date of Patent: Nov. 28, 1995

[54] CONTINUOUS, STEADY-STATE, CHROMATOGRAPHIC SEPARATION OF GADOLINIUM ISOTOPES

[75] Inventors: Thomas S. Snyder, Oakmont; Steven H. Peterson; Umesh P. Nayak, both of Murrysville, all of Pa.

[73] Assignee: Westinghouse Electric Corporation, Pittsburgh, Pa.

[21] Appl. No.: 264,806

[22] Filed: Jun. 23, 1994

[51] Int. Cl.$^6$ .................................................. B01D 15/08
[52] U.S. Cl. ........................ 210/635; 210/656; 210/657; 210/659; 210/198.2; 423/215; 423/263; 423/DIG. 7
[58] Field of Search ................................. 210/635, 656, 210/659, 198.2, 657; 423/21.1, 21.5, 263, DIG. 7

[56] References Cited

U.S. PATENT DOCUMENTS

| | | | |
|---|---|---|---|
| 3,582,263 | 6/1971 | Chiola et al. | 23/22 |
| 3,615,173 | 10/1971 | Winget | 423/21.5 |
| 4,394,353 | 7/1983 | Miyaka et al. | 423/21.5 |
| 4,438,078 | 3/1984 | Nalewajek | 423/21.5 |
| 4,514,367 | 4/1985 | Asami et al. | 423/21.5 |
| 4,711,768 | 12/1987 | Peterson et al. | 423/21.5 |
| 4,915,843 | 4/1990 | Taniguchi | 210/659 |
| 5,024,749 | 6/1991 | Snyder | 210/198.2 |
| 5,045,209 | 9/1991 | Snyder et al. | 210/656 |
| 5,098,678 | 3/1992 | Lee et al. | 423/70 |
| 5,110,566 | 5/1992 | Snyder et al. | 423/70 |
| 5,124,023 | 6/1992 | Bosserman | 210/659 |
| 5,133,869 | 7/1992 | Taniguchi | 210/659 |
| 5,174,971 | 12/1992 | Snyder et al. | 423/70 |

OTHER PUBLICATIONS

R. C. Vickery, *Chemistry of Lanthanides*, Chapter 11—"Complete Separational Scheme", pp. 175–196, Academic Press, N.Y., N.Y. (1953).

J. B. Walker, et al., *Lanthanide/Actinide Chemistry*, Chapter 10–"Thermodynamic Parameters of Fluoride Compexes of the Lanthanides", pp. 127–140, Am. Chem. Soc., Adv. Chem. Series 71, N.Y., N.Y. (1966).

Lucy, et al., Determination of Trace Lanthanide Impurities in Nuclear Grade Uranium By Coupled–Column Liquid Chromatography, pp. 3320–3325, Anal. Chem., vol. 65, No. 22 (Nov. 15, 1993).

*Primary Examiner*—Ernest G. Therkorn

[57] ABSTRACT

A method and apparatus for the partial or complete continuous separation of isotopes of gadolinium, especially high thermal neutron capture cross-section gadolinium isotopes, using continuous, steady-state, chromatography in which an ion exchange resin is the stationary phase, an aqueous solution of ions based on a mixture of gadolinium isotopes is the feed phase, and an aqueous acid eluant solution is the mobile phase. The method involves the mobile phase eluting or desorbing the gadolinium isotopic solute or ligand adsorbed on the stationary phase under conditions such that each of the various naturally occurring isotopes of gadolinium is primarily eluted in an elution volume distinct from the elution volumes of the other isotopes. In a preferred embodiment, the conditions are such that at least one of the elution volumes contains essentially only one isotope of gadolinium. The method is preferably conducted in a continuous, steady-state manner, and it is preferably conducted in a single operation in a continuous annular chromatograph (CAC).

16 Claims, 9 Drawing Sheets

GRAPH CALCULATIONS:
GADOLINIUM ISOTOPE SEPERATION ON CONTINUOUS ANNULAR CHROMATOGRAPH, CAC
7 ISOTOPES OF Gd:
  i: = 1.. 7

| $MASS_i$: = | $ABUNDANCE_i$: = | $\sigma_i$: = |
|---|---|---|
| 152 | .2 | 1100 |
| 154 | 2.15 | 85 |
| 155 | 14.73 | 61000 |
| 156 | 20.47 | 1.5 |
| 157 | 15.68 | 254000 |
| 158 | 24.87 | 2.5 |
| 160 | 21.9 | .77 |

SEPERATE ISOTOPE BANDS CHROMATOGRAPHICALLY, ACCORDING TO:
  R: = 10     R IS A SCALING FACTOR THAT DESCRIBES SEPERATION OF BANDS.
CENTER(R,i): = R·($MASS_i$ − 152)

| $MASS_i$ | CENTER(R,i) |
|---|---|
| 152 | 0 |
| 154 | 20 |
| 155 | 30 |
| 156 | 40 |
| 157 | 50 |
| 158 | 60 |
| 160 | 80 |

ASSUME THAT BANDS FORM GAUSSIAN CONCENTRATION DISTRIBUTIONS ALONG ELUTION DIRECTION.

$$CONC(i,x): = \frac{1}{20\sqrt{2\cdot\pi}} \cdot ABUNDANCE_i \cdot EXP\left[-\frac{(CENTER(R,i) - x)^2}{40}\right]$$

THE CONCETRATION OF EACH ISOTOPE ALONG THE SPATIAL VARIABLE x CAN BE SHOWN:
  x: = 0.. 150

CONTINUOUS, STEADY-STATE, CHROMATOGRAPHIC SEPARATION OF GADOLINIUM ISOTOPES

FIELD OF THE INVENTION

The present invention relates; to the field of rare earth elements, and more particularly to the separation of isotopes of rare earth elements. Even more particularly, the invention relates to a method and apparatus for the selective separation of gadolinium isotopes having high neutron capture cross-section from a mixture of other gadolinium isotopes or from a mixture of other gadolinium isotopes and other rare earth elements.

BACKGROUND OF THE INVENTION

The rate of nuclear fission reactions in nuclear reactors are a function of the number of neutrons available to carry on the neutron triggered chain reactions. The fission of a fuel nucleus releases one or more neutrons, and one neutron is required to sustain the chain reaction. Many of the design features of a nuclear reactor are based upon their impact on the neutron economy. In particular, materials for use in nuclear reactors are selected for their neutron capture cross-sections, $\sigma$, along with other properties. Low $\sigma$ materials are selected for most reactor components, such as support structure, fuel rod cladding, moderators, and the like. Whereas, high $\sigma$ materials are selected for control rods and burnable poison shims. The more transparent the internal materials of construction of a nuclear reactor are to such thermal neutrons, the more efficiently the reactor will function since a certain number of these neutrons are necessary to sustain the nuclear reaction. A "burnable poison shim" is a high $\sigma$ material added in a carefully selected quantity to decrease neutron flux early in a fuel cycle, and to become transparent or neutral after neutron adsorption so that late in a fuel cycle more of the fission neutrons are absorbed by fuel.

Gadolinium (Gd) is a rare earth element which finds its greatest potential application as a neutron absorber in a nuclear reactor. Gadolinium has historically been a material of construction for nuclear reactor control rods. In such applications, it serves its function by absorbing thermal neutrons having an average thermal neutron capture cross-section of about 49,000 barns ($10^{-24}$ cm$^2$). However, some isotopes of gadolinium are much more efficient at neutron capture because of their much greater thermal neutron capture cross-sections, $\sigma$.

Gadolinium is the element with the highest $\sigma$ for its natural isotope mixture. Only two isotopes of gadolinium, $Gd^{155}$ and $Gd^{157}$, are particularly attractive as having high neutron capture cross-sections as shown in the following Table 1 which is an approximation of the distribution of the naturally occurring gadolinium isotopes.

TABLE 1

| Naturally Occurring Gadolinium Isotopic Distribution | | |
| --- | --- | --- |
| Isotope Mass No. | Natural Atomic % | Thermal Neutron Capture Cross-Section $\sigma$ (Barns) |
| 152 | 0.20 | 1100 |
| 154 | 2.15 | 85 |
| 155 | 14.73 | 61,000 |
| 156 | 20.47 | 1.5 |
| 157 | 15.68 | 254,000 |
| 158 | 24.85 | 2.5 |
| 160 | 21.90 | 0.77 |

As illustrated, $Gd^{155}$ and $Gd^{157}$ have the highest thermal neutron capture cross-sections $\sigma$ but comprise only about 30 percent of the natural gadolinium. There is a need, therefore, to separate the high neutron capture Gd isotopes from the other Gd isotopes and also from other rare earth elements. There is a need for a technique which could simultaneously isolate the high neutron cross-section $Gd^{155}$ and $Gd^{157}$ isotopes from a mixture of other Gd isotopes.

Figure 1A:
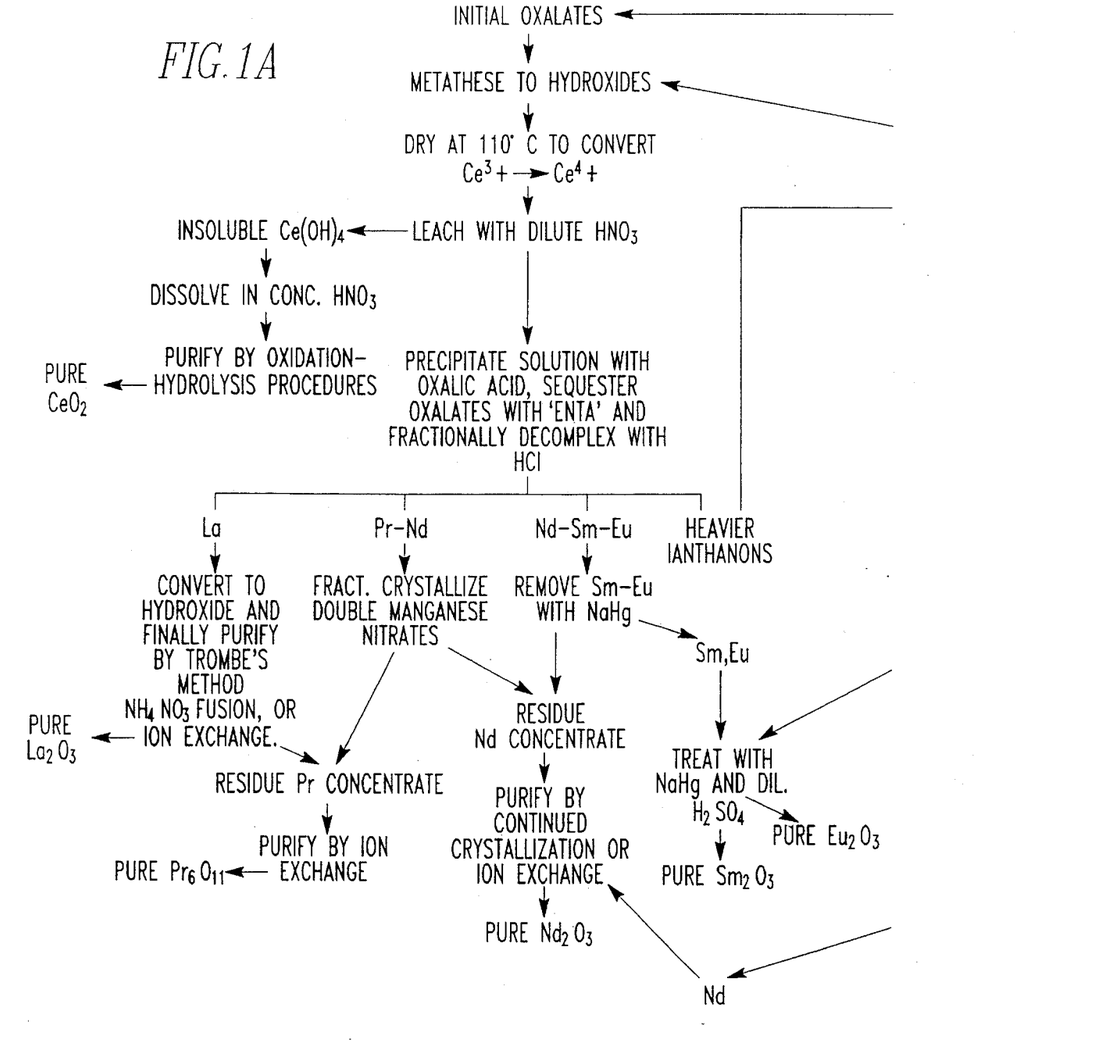
FIGS. 1A and 1B, is a diagram of a conventional lanthanide separation scheme.
Figure 1B:
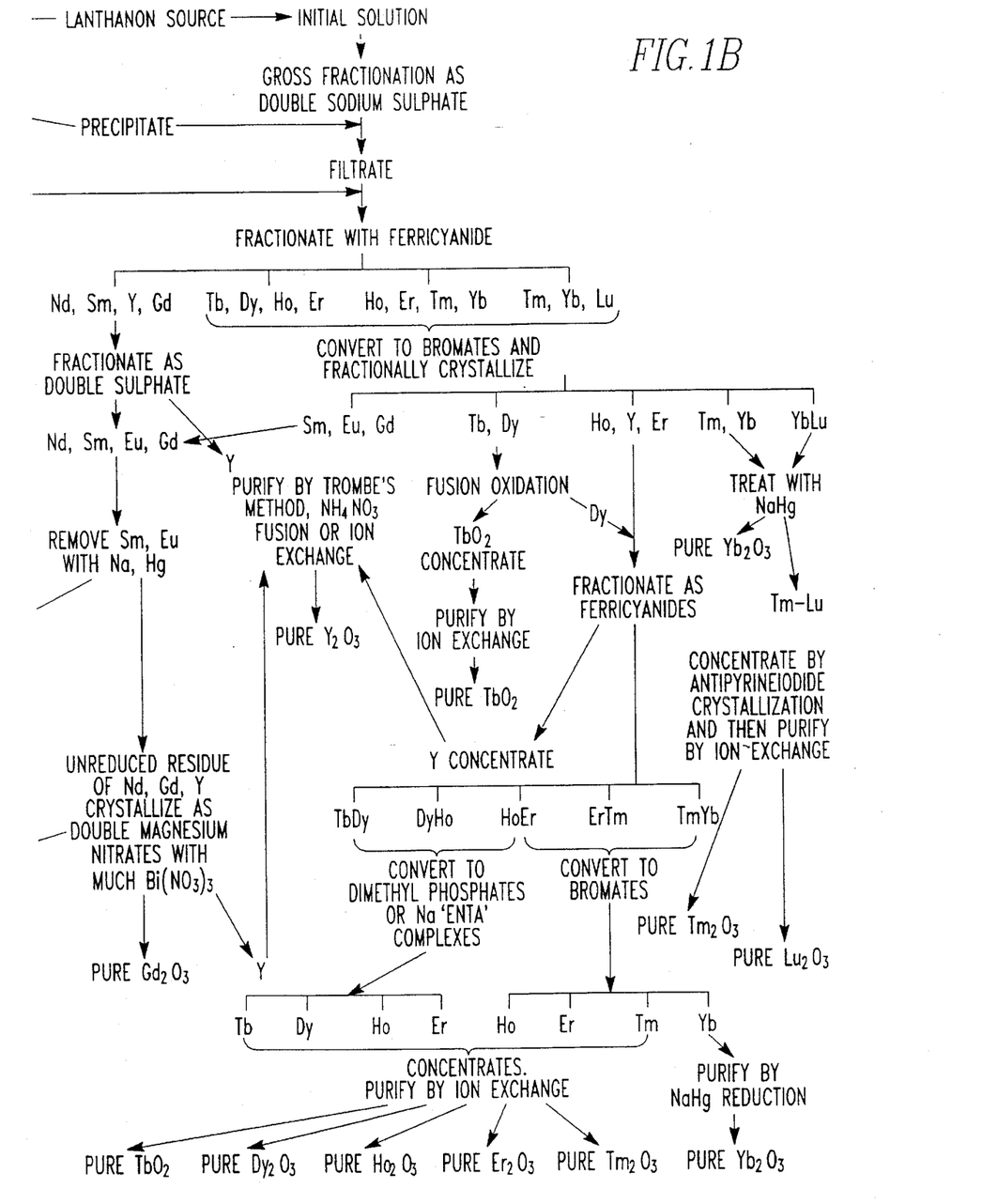

As shown by the separation schemes in FIG. 1, the separation of gadolinium from other lanthanides (i.e., La, Ce, Pr, Nd, Pm, Sm, Eu, Gd, Tb, Dy, Ho, Er, Tm, Yb, and Lu) is a complex issue. Different chemistries are required for various fractionation operations of the individual lanthanides, since no two lanthanides have identical chemistries. The kinetics of separations also differ which implies a kinetically driven, rather than equilibrium driven, separation operation. In addition, the chemistries for performing isotopic enrichment, i.e., separation of isotopes and purification, from the individual fractions will also differ and require different isotope enrichment schemes. For example, as shown in FIG. 1, gadolinium separation proceeds better in nitrate systems while erbium separation proceeds better in phosphate and ferricyanide systems.

Much of the difference is due to the basic differences in the electronic configuration of various elements which manifest themselves in different hydrolytic and complex formation behavior and, accordingly, influence the separation behaviors of these elements, such as in ion exchange separations. The acidity of lanthanides will increase in the order of decreasing ionic radii as defined by the electronic configuration of the elements. Acidity is an important property that determines the ion exchange behavior; for example, as Gd hydrates in water it tends to displace a hydrogen ion from a water molecule of hydrolysis. Moreover, Gd is a trivalent species and will tend not to form stable complexes with anionic species in solution. Gd typically will go into solutions as a cation and stringent solution concentrations are required to form its anionic complexes.

Ion exchange separation schemes involve both complex formation and hydrolysis formation phenomena. In cation exchange, $H^+$ is liberated and in anion exchange, $OH^-$ is liberated from the ion exchange media. The atomic radii of lanthanides increases with atomic number. The smaller radii-elements are typically absorbed as cations on cationic ion exchange resins preferentially, and the smaller radii elements are then eluted from the cationic ion exchange resin with a solution containing a strongly complexing anion, such as citric acid. It is expected that individual fractionation and isotopic separation will occur differently with different elements.

Prior efforts at isotope separation have involved some type of solvent extraction. But these separation techniques are generally only able to separate only one isotope at a time, and, therefore, require a plurality of extraction trains and purification steps. Other efforts for simultaneous separation of isotopes other than gadolinium using ion exchange in a continuous annular chromatograph are taught in U.S. Pat. Nos. 5,098,678 (Lee, et al.), 5,110,566 (Snyder, et al.) and 5,174,971 (Snyder, et al.).

Recent efforts of separating gadolinium from its isotopes and also from other rare earth elements have been focused on ion exchange chromatography. U.S. Pat. No. 4,711,768 (Peterson, et al.) teaches a method of separating gadolinium isotopes, i.e., $Gd^{155}$, $Gd^{156}$ and/or $Gd^{157}$, from mixtures containing the same by a batchwise chromatographic process using a plurality of liquid chromatographic columns, an ion exchange resin stationary phase and an eluant solution mobile phase, and sequentially separating the isotopes one at a time.

It is difficult to effect a good separation using traditional chromatography due to problems associated with controlling the elution of isotope product peaks. Consequently, it is difficult to get the concentration of gadolinium isotope in the product of elution as high as desired. Thus, larger than desired volumes of spent eluant must be used which poses a waste management problem. In addition, this batchwise approach is both expensive to build and difficult to control. There is a need to concurrently or simultaneously separate the high thermal neutron capture cross-section Gd isotopes, especially $Gd^{155}$ and $Gd^{157}$, in a continuously operating ion exchange chromatographic separation technique while also using reduced elution volumes.

SUMMARY OF THE INVENTION

It is an object of the present invention to provide a method and apparatus for separating desired gadolinium isotopes from a mixture of other gadolinium isotopes.

It is an object of the present invention to provide a method and apparatus for separating desired gadolinium isotopes from a mixture of other gadolinium isotopes and other rare earth elements.

It is a further object of the present invention to provide a method and apparatus for simultaneously separating gadolinium isotopes from other rare earth elements and isolating the $Gd^{155}$ and $Gd^{157}$ isotopes, i.e., the isotopes with the greatest thermal neutron capture cross-sections, from other gadolinium isotopes.

It is yet another object of the present invention to provide a continuous, steady-state, method and apparatus for separating the isotopes of gadolinium using a continuously operating chromatographic technique, and further reducing the volume of waste liquor.

It is an advantage of the present invention to provide larger separation factors by using a continuous chromatographic technique.

These and other objects and advantages are accomplished by a method and apparatus for the partial or complete separation of isotopes of gadolinium using chromatography in which an ion exchange resin is the stationary phase, an aqueous solution of ions based on a mixture of gadolinium isotopes is the feed phase, and an aqueous acid eluant solution is the mobile phase. The method involves the mobile phase eluting or absorbing the gadolinium isotopic solute or ligand adsorbed on the stationary phase under conditions such that each of the various naturally occurring isotopes of gadolinium is primarily eluted in an elution volume distinct from the elution volumes of the other isotopes. In a preferred embodiment, the conditions are such that at least one of the elution volumes contains essentially only one isotope of gadolinium. The method is preferably conducted in a continuous, steady-state manner, and it is preferably conducted in a continuous annular chromatograph (CAC).

A particularly preferred embodiment involves feeding a gadolinium compound dissolved in an aqueous acid to a continuous annular chromatograph (CAC) with a stationary phase of an ion exchange resin. The mobile phase is preferably aqueous acid, more preferably nitric acid ($HNO_3$), but also sulfuric acid ($H_2SO_4$), hydrochloric acid (HCl), phosphoric acids, butyric acids ($C_4H_8O_2$), oxalic acid ($C_2H_2O_4$), citric acid ($C_6H_8O_7$), and acid halides (e.g., HF) or the like. The stationary phase is preferably a cationic ion exchange resin due to the typical trivalent nature of gadolinium; however, due to the multivalent behavior of gadolinium, an anionic exchange resin can also be used depending on the eluant or mobile phase acid strength and the complexes in solution.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings, FIG. 1, including

FIG. 8, including

DETAILED DESCRIPTION OF THE PREFERRED EMBODIMENTS

The method and apparatus according to the present invention effects the efficient and economical separation of high thermal neutron capture cross-section gadolinium isotopes from mixtures containing gadolinium isotopes. Of particular interest is the continuous separation and isolation of $Gd^{155}$ and $Gd^{157}$ isotopes concurrently in a single operation.

The mixture that is treated according to the present invention can comprise a mixture of gadolinium isotopes that has previously been separated from other rare earth metals, or can also comprise a mixture of gadolinium isotopes and other rare earth metals, such as, for example, La, Ce, Pr, Nd, Sm, Eu, Tb, Dy, Ho, Er, Tm, Yb, Lu, Y lanthanides or the like. The separation of desired gadolinium isotopes is preferably effected by using a saturated anionic or cationic ion exchange resin which is the stationary phase, an aqueous solution of an ionic compound of a mixture of gadolinium isotopes which is the feed phase, and an aqueous acid eluant solution which is the mobile phase.

The starting material or feed phase used in the method according to the present invention can comprise a feed solution of a mixture of gadolinium isotopes or oxides thereof that are converted to ions in aqueous solution, for example, by dissolving the mixture of gadolinium ions in nitric acid or other strong mineral acids, such as hydrochloric acid, sulfuric acid, butyric acid, or phosphoric acid or mixtures thereof. The feed phase is, therefore, any convenient solution of ionic gadolinium compounds formed from a mixture of gadolinium isotopes. The isotope mixture may be that which occurs in nature or it may be a partially refined mixture obtained from a preliminary refinement process.

It is preferred that the feed phase have a concentration of gadolinium as high is possible without exceeding the solubility limit for the solute under the anticipated operating conditions. The natural consequence of chromatographic separation is a dilution of the concentration of the products being separated into product streams. Therefore, the overall efficiency of the process and particularly a minimization of the efforts needed to recover the desired products from the product streams is best served by using as high a concentration as possible without creating an undue risk that gadolinium will precipitate out during the course of the process. It is particularly preferred to use a gadolinium concentration in excess of about 0.1 to 1 molar in the feed phase, preferably about 2 to 5 molar, even more preferably near the solubility limit of the feed phase. The CRC *Handbook of Chemistry and Physics* lists $Gd(NO_3)_3$, $GdCl_3$, and $Gd_2(SO_4)_3$ as soluble.

The stationary phase can be any anion or cation exchange resin having an affinity for gadolinium ions. It is preferred that the stationary phase is a cation exchange resin with an affinity for gadolinium ions, typically in aqueous solution as a $Gd^{3+}$ cation, but which may also be complexed with $NO_3^-$, $Cl^-$, $SO_4^{2-}$, $PO_3^-$ or other anions depending on the acid solvent. A preferred feed phase is that obtained by hydrolyzing gadolinium oxide ($Gd_2O_3$) in nitric acid ($HNO_3$). It is preferred that the ion exchange resin be capable of displaying a strong affinity for the gadolinium ion in the feed phase.

Preferred cation exchange resins are those based on active groups of nitrates, carboxylates, phosphates, carbonates and hydroxides. Preferred anion exchange resins are those based on active groups of ammonium groups derived from primary and tertiary amines and the quartenary ammonium groups. Especially preferred groups are those derived from tricapryl methyl ammonium chloride, tri-n-octyl amine and primary amine. The solid matrix of these cation and anion exchange resins are typically porous polystyrene resins or porous zeolite structures. A more detailed description of cationic and anionic ion exchange resins which can be used in the invention can be found in *Perry's Chemical Engineers' Handbook*, Sixth Edition, pp. 16-1 to 16-48 and Table 16-4 (1984), hereby incorporated by reference herein.

It is also preferred that the ion exchange resin stationary phase be capable of displaying a high ionic capacity for such ions per unit volume as reflected by a large solid to liquid distribution coefficient defined as $K_d = C_{resin}/C_{liquor}$, in dilute mineral acid solutions. It is particularly preferred to use ion exchange resins with the highest capacities possible, typically between about 0.01 and 0.5 milliequivalents per milliliter with the most probable capacity of about 0.1 milliequivalents per milliliter under elution conditions. These ratings are based upon resins with bead sizes in the 500 micron range and are based on the ability to bind free acid.

The smaller bead size preferred by the present invention will yield more surface area per unit volume and consequently a higher actual capacity. On the other hand, the affinity of the resin for gadolinium ions may differ from its affinity for free acid ions. The ultimate criteria is simply whether the resin can yield a reasonable separation factor, $\alpha$, under practical chromatography conditions. However, the higher the general ionic capacity of a resin, the more readily it can be adapted for use in the present invention.

It is also preferred that the stationary phase comprise a narrow monodisperse distribution of spherical particles with a small average particle size. Deviations in particle size make it more difficult to get efficient separation. Thus, a polydisperse particle size distribution will require a longer column length and result in more dilute product fractions because a larger range of eluant volumes will contain desired product. The separation efficiency can also be enhanced by lowering the particle size range of the monodisperse distribution. A small average particle size is preferred because the exchange reaction is a phenomenon which occurs at the surface of the ion exchange resin beads of the stationary phase. Thus, separation efficiency is enhanced by maximizing the surface to volume ratio of the ion exchange resin beads. However, this needs to be balanced by the effect which decreasing the particle size has on the permeability of the stationary phase and has on retaining the beads in the column. An especially preferred particle size is between about 0.1 and 10 microns.

The mobile phase or eluant may be aqueous acid solution capable of solvating the gadolinium ions such that they can be eluted down the column. This mobile phase or eluant is a fluid capable of displacing the gadolinium ions from the ionic association with the stationary phase. It is preferably an aqueous solution of a strong mineral acid such as nitric acid, and can also include other strong mineral acids such a hydrochloric acid, sulfuric acid, butyric acid, phosphoric acid, citric acid, oxalic acid, acid halides (e.g. fluoro acids) or mixtures thereof. Particularly preferred are sulfuric acid and hydrochloric acid and nitric acid, with nitric acid being especially preferred. The acid strength needed is dependant on the identity of particular acid utilized but acid strengths of about 1 normal or greater are preferred.

The mobile phase is preferably an aqueous acid at a strength somewhat lower than that of the feed phase. Preferably, the mobile phase has a acid concentration between about 0.1 and 1 normal when the feed solution has an acid strength of about 1 normal or greater. The precise acid strength needed will depend upon the nature of the ion exchange resin's active groups and the identity of the eluant acid. The mobile phase can be reused if recovered from the gadolinium product fractions and deionized by conventional techniques.

The effective column height should be sufficient to allow significant resolution of the various isotopes of gadolinium, especially $Gd^{155}$ and $Gd^{157}$, into distinct product fractions. The resolution is preferably sufficient to yield an isotope purity in excess of 50%, preferably in excess of about 90%, even more preferably at least about 98%. It is preferred that this resolution be effected in a single pass through the column. The effective column height needed for a given resolution can be estimated from an application of the Kremser-Brown-Saunders equation to empirical data on a separation capacity of a given stationary phase, mobile phase, eluant and flow conditions.

A fundamental quantity $\alpha$ (alpha) exists in all stochastic separation processes, such as chromatographic separation processes, as an index of the steady-state separation that can be attained in an element of the process equipment. The separation stage, or in a continuous separation process, the transfer unit or equivalent theoretical plate, may be considered as a device separating a feed stream or streams into two effluent streams, often called "heads" and "tails", or product and waste. The quantity relates the concentrations of the components in the two effluent streams. For the case of separation of a binary mixture, a separation factor, $\alpha$, is used to define the ability to separate the various gadolinium isotopes. This factor is itself defined by Equation (1) for the binary case.

$$\alpha = \frac{y/(1-y)}{x/(1-x)} \quad (1)$$

where y is the molar concentration of the desired isotope in the product fraction rich in that isotope or "heads" stream and x is the molar concentration of the same isotope in the "tails" stream from the state. Approximate calculations can be performed by selecting one isotopic fraction as the desired product or heads fraction, and defining the tails fraction as the composite of the other product fractions. Thus, if a product fraction is obtained in which 98% of the gadolinium is $Gd^{155}$ and if in the composite of all the other product fractions together only 2% of the gadolinium is $Gd^{155}$, the $\alpha$ defining the separation would be:

$$y = 0.98;$$
$$x = 0.02;$$

$$\alpha = \frac{0.98(0.98)}{0.02(0.02)} = 2401;$$

mole fraction of $Gd^{155}$ in natural Gd = 14.73%.

Separation factors, $\alpha$, for isotopic separations are conveniently evaluated on 25 to 100 cm columns with a 25 cm length being preferred. For such columns $\alpha$ values for the desired isotope, for instance, $Gd^{155}$, on the preferred stationary phases with the preferred eluants are greater than about 1.05, preferably greater than about 1.085. In general, for a commercially acceptable gadolinium enrichment process, $\alpha$ ranges should be from about 1.01 to about 1.10.

The effective column length required for any desired degree or purification is then determined from this data. For instance, if a 25 cm test column yields a separation factor, $\alpha$ of 1.085, this can be used as the separation factor for a theoretical stage, $\alpha_s$, in applying the Kremser-Brown-Saunders Equation (2) for estimating the number of theoretical stages, N, required.

$$N = \frac{\ln \alpha_T}{\ln \alpha_S} \quad (2)$$

For the case being discussed this yields the following result:

$$N = \frac{\ln 2400}{\ln 1.085} = 95$$

Thus, 95 theoretical stages of 25 cm each are required which implies an effective column length of about 24 meters. This is based on the assumption that the Kremser-Brown-Saunders equation holds in the Underwood-Fenske form assuming the binary mixture approximation.

The following Table 2 shows projected column length as a function of $\alpha$ and desired product purity for 90% separation and recovery of the high thermal neutron capture cross-section gadolinium isotopes (i.e., $Gd^{155} + Gd^{157}$ isotopes) from the other gadolinium isotopes.

TABLE 2

| Purity (%) | 98% | 95% | 50% |
|---|---|---|---|
| Heads (kg/kg) | 0.279 | 0.288 | 0.547 |
| Tails (mole frac.) | 0.042 | 0.043 | 0.067 |
| $\alpha$ | 1113 | 426 | 14 |

| $\alpha$ for 0.25 m Test Column | Number of Stages | Total Column Length (m) | Number of Stages | Total Column Length (m) | Number of Stages | Total Column Length (m) |
|---|---|---|---|---|---|---|
| 1.001 | 7018 | 1755 | 6057 | 1514 | 2633 | 658 |
| 1.01 | 705 | 176 | 608 | 152 | 264 | 66 |
| 1.03 | 237 | 59 | 205 | 51 | 89 | 22 |
| 1.09 | 81 | 20 | 70 | 18 | 31 | 8 |
| 1.10 | 74 | 18 | 64 | 16 | 28 | 7 |

The effective column height can be vertical but it may have other orientations. What is important is the effective path over which the mobile phase travels.

It is preferred that the path be provided in such a way that the chromatographic separation can be operated continuously. There is no convenient technique currently available for instantaneously sensing the concentration of any given isotope of gadolinium. Thus, there is a preference for a continuously operating procedure which has reached steady-state so that a particular product fraction reproducible has a certain isotope distribution. If the chromatographic separation is affected in a discontinuous or batch manner, then random variations between runs may make it difficult to reproducibly collect product fractions with the same isotope distribution from run to run. For instance, if a single vertical column is loaded in a batch manner, the elution time of the product fraction rich in a particular isotope may vary from run to run due to random variables difficult to control such as feed concentration fluctuations, etc.

A particularly preferred continuously operating chromatograph is the continuous annular chromatograph (CAC). This device was developed by Oak Ridge National Laboratory and comprises an annular stationary phase which is rotated about the axis of the annulus. The annulus is provided by packing the stationary phase material, such as resin beads, between two concentric cylinders of different diameters with vertical axes. A feed port is provided at a given angular position and at one or more eluant ports are provided at some angular offset position from the feed port. It is preferred to place a layer of glass beads above the stationary phase, and to feed the eluant onto the top of the glass bead layer while feeding the gadolinium feed phase directly onto the top of the stationary phase by having its feed nozzles or nozzle extending through the glass bead layer. This should prevent any undesired mixing effects.

This CAC device is provided with a number of product ports set at a number of angular positions which can be set arbitrarily to accommodate a particular set of operating conditions. Each product port collects an elution volume which has had a particular residence time on a column. The stationary phase is typically rotated at a constant speed so that any vertical segment of the annular bed is above a particular fixed product collection port at a given time after the segment has been loaded with gadolinium feed stock and eluant. Thus, each product collection port has an angular position which corresponds to a particular elution time for a particular rate of rotation of the stationary phase for a particular flow rate through the stationary phase.

The flow rate through the stationary phase is controlled by the pressure drop across the effective height of the stationary phase and the physical characteristics of the stationary phase, i.e., particle size and packing void volume. This pressure drop may be provided by the hydrostatic head of the feed phase and eluant but is preferably provided by pressurizing the CAC device. The pressure required to achieve a particular flow rate is governed by the nature of the stationary phase, i.e., by its packing, average particle size, and particle size distribution. Thus, the smaller the average particle size of the resin beads making up the stationary phase results in the larger pressure drop required to obtain a particular flow rate over a particular effective height. However, the separation factor $\alpha$ for any given theoretical stage is improved as the average particles size of the resin beads is decreased. Thus, the effective height needed to effect a given degree of separation is decreased as a separation capacity of a unit length, or, in other words, theoretical stage height, is decreased by decreasing the average particle size of the resin beads.

The flow rate across the effective height of the stationary phase and a rotational speed of a stationary phase should be coordinated such that a particular product fraction always elutes at the same angular position, and, thus, is always delivered to the same product collection port.

It is preferred that the isotope separation chromatograph be operated in a displacement mode wherein no more than about 5%, more preferably no more than about 1% of the effective column height, is loaded with feed phase before elution is initiated. This is conveniently effected by using a feed solution which is unable to release the ions of interest from the ionic bonding with the ion exchange resin and loading no more than about 5%, preferably about 1% of the effective height, before adding an eluant of suitable strength to cause the anions to migrate down the column at a reasonable rate. In the continuous annular chromatograph (CAC) this end is achieved by coordinating the angular displacement between the feed port and the eluant port and the speed of rotation of the annular bed so that the time interval between loading and elution is just sufficient for the desired degree of penetration. The relationship between the time for loading and the depth of penetration is in turn governed by the flow rate through the annular bed.

The displacement may be effected by either an isocratic or a gradient supply of eluant. In the former case, the eluant can simply be supplied from a single port while in the latter case, several ports at successively greater angular displacements from the feed port are utilized. In the gradient mode, elution under the influence of initial eluant is permitted to proceed until some separation of the isotopes of interest has been effected and then a more effective eluant is supplied. This increases the migration speed of these isotopes down the column and minimizes the range of elution volumes or times over which a given component or product fraction will exit the column, or, in other words, this procedure minimizes the band spreading.

Decreasing the elution volumes by gradient elution or by other means increases the concentration of the product, for example, the gadolinium isotope, in the product fraction. It is preferred to maximize the concentration of product, thereby reducing the total volume of fluid to be processed. This allows for a reduction in the overall size of the system with a consequent reduction in capital and operating expenses. However, practical consideration such a solubility limits constrain the maximum concentrations obtainable.

The flow rate down the column is governed by the pressure drop from the top to the bottom of the column and the nature of the stationary phase. The smaller the average particle size of the resin beads making up the stationary phase the higher the pressure drop required to obtain a given-flow rate. This relationship is also effected by the particle size distribution of these resin beads. There is, however, a maximum attainable flow rate for any given anion exchange resin stationary, phase which cannot be exceeded by the application of additional pressure. The suppliers of such resins rate them in terms of flow rate per given pressure drop and maximum attainable flow rate.

It is preferred to use a stationary phase which will permit flow rates between about 2 and 80, more preferably between about 3 and 20 gallons per minute per square foot of cross-sectional area (between about $1.36 \times 10^{-3}$ and $5.43 \times 10^{-2}$ m$^3$/sec, more preferably between about $2.04 \times 10^{-3}$ and $1.36 \times 10^{-2}$ m$^3$/sec per square meter of cross-sectional area). There is a relationship between the achievable flow rates and the effective column height needed for a given degree of purity. For a given system of stationary phase and eluant, the theoretical stage separation factor, $\alpha_s$, of the stationary phase for any isotope of interest will increase as the average particle size of the resin beads of the stationary phase decreases. However, as this particle size decreases, so does the flow capacity of the stationary phase. Thus, there is an inverse relationship between $\alpha_s$ and the flow capacity. Therefore, a higher flow rate will require a greater effective column height to achieve to the degree of separation or product fraction purity.

Furthermore, there is the additional constraint that the pressure required to achieve the desired flow rate not exceed the capability of available pumps, seals and feed tubing. The required pressure is a function of both the pressure drop needed per unit of effective height and the total effective height required for the desired degree of separation. Thus, as the flow capacity of the stationary phase is increased by a change in the physical configuration and consequently its theoretical state separation factor, $\alpha_s$, is decreased, the required effective height and a required overall pressure drop are both increased. On the other hand, as theoretical state separation factor, $\alpha_s$, is increased by a change in the resin bead size distribution and consequently the flow capacity of the stationary phase is decreased, the pressure drop for a given effective height is increased. A pressure drop of less than about 400 psi, more especially between about 50 and 100 psi is preferred.

Thus, to obtain a system with a commercially practical capacity, it is necessary to use a stationary phase which will simultaneously display both a reasonable theoretical stage separation factor, $\alpha_s$, and a reasonable flow rate per unit of effective height with a reasonable pressure drop. This can be achieved by an appropriate selection of both the ionic capacity of the stationary phase ion exchange resin and the eluant.

In a preferred mode, several product collection ports are used to collect a particular product fraction. This is accomplished by closely spacing these collection ports so that they more than span the angular range of rotation that corresponds to the elution time interval of that particular fraction but do not extend to the angular positions at which any significant portion of any other product fraction is expected to elute. Of course, this requires that the elution time intervals or different product fractions do not substantially overlap. This arrangement tends to insure that minor fluctuations in the steady-state elution behavior which could cause a slight advancement or retardation of the elution time of the desired product fraction will not result in any loss of this fraction.

The chromatograph may be configured to separate just the isotopes of gadolinium from a mixture of gadolinium isotopes or to also separate the isotopes of gadolinium from a mixture of gadolinium isotopes and other rare earth metals. Of course, if the elemental separation is effected in one column and the isotopic separation or separations in another, the operating conditions in each column may be optimized with regard to the functions of that column.

A particularly preferred device for use in practicing the method according to the present invention is illustrated in FIGS. 2 through 6. The continuous annular chromatograph 10 (CAC) shown in FIG. 2 comprises two concentric cylinders 30 and 35 which define the annular space 32 seen in FIG. 2. Atop this annular space 32 is a distributor plate 20. Feed pipes or channels 21 and 23 run through the distributor plate 20 and terminate in feed nozzles 22 and 24, respectively. The feed nozzles 22 are intended to supply the feed phase to the exchange resin beads 27 which are packed in the annular space 32. For ease of illustration, these beads are shown as only partially filling the annular space 32. On the other hand, the feed nozzles 24 are intended to feed the eluant to the layer of glass beads 26 which sits atop the exchange resin beads 27. The feed nozzles 24 are somewhat shorter than the feed nozzles 22. This feed arrangement serve to avoid any back mixing of the feed phase.

Figure 2:
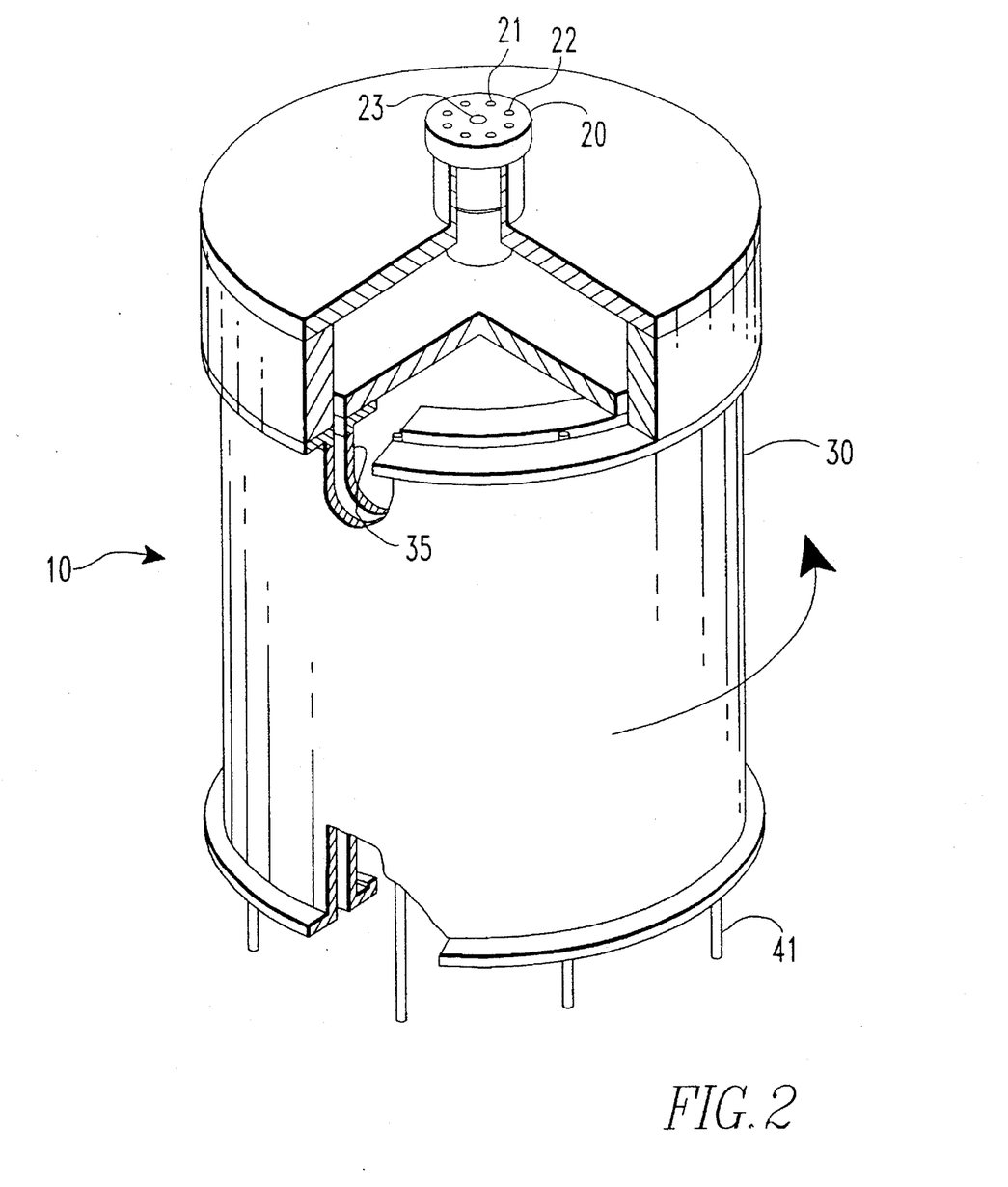
FIG. 2 is a perspective view of a continuous annular chromatograph (CAC) with a portion in section to illustrate the annular construction.
Figure 3:
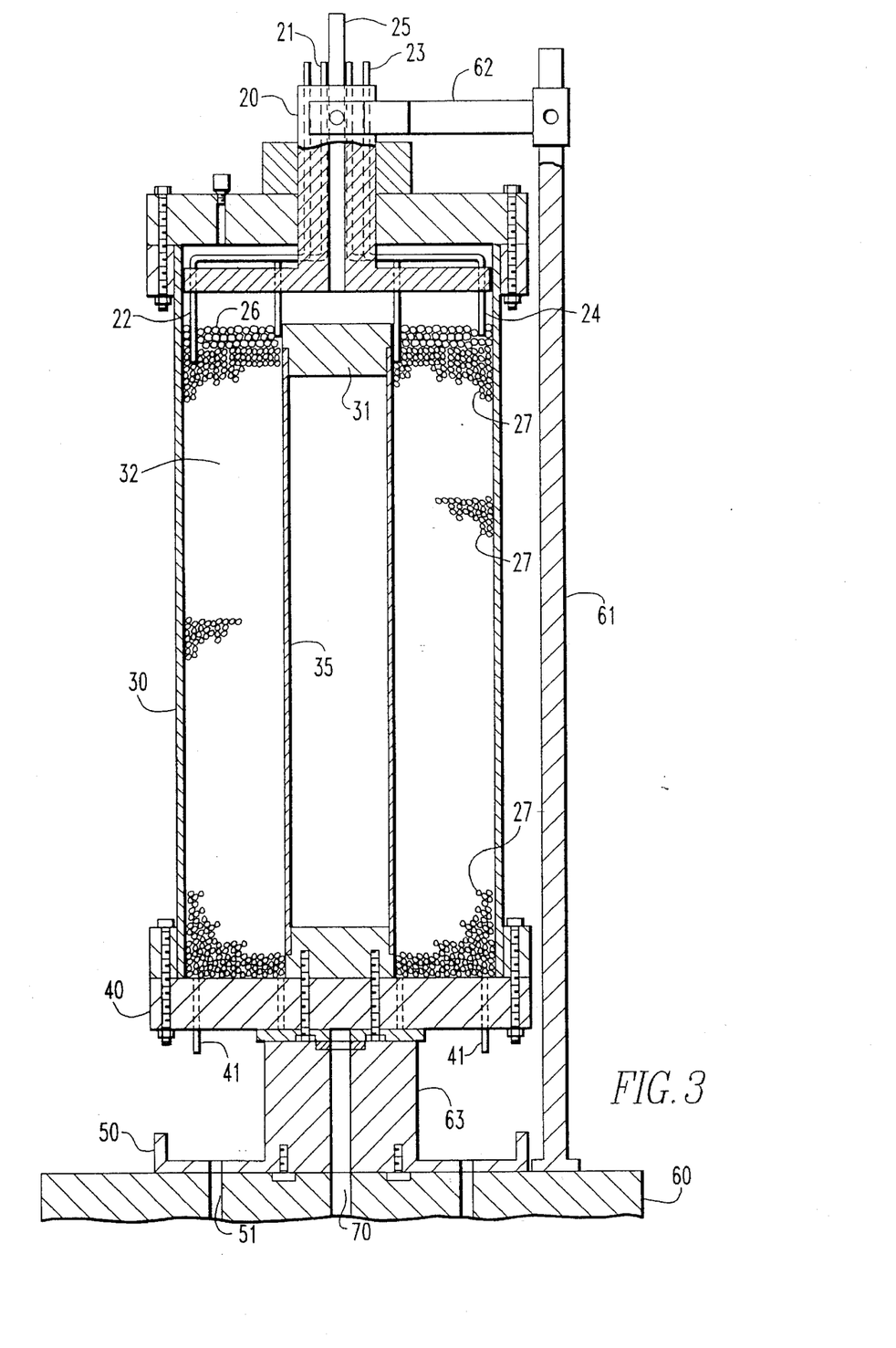
FIG. 3 is a horizontal sectional view of the CAC along a diameter of the concentric circles defining the annulus.
Figure 4:
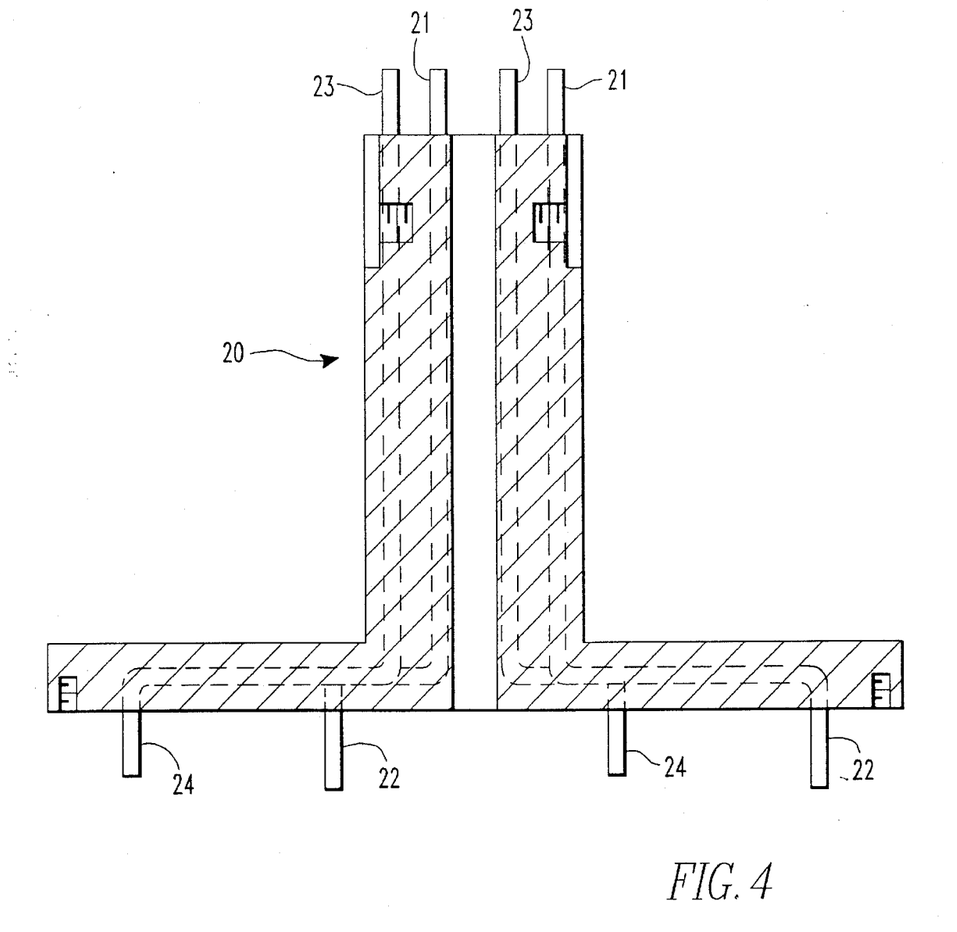
FIG. 4 is an enlarged horizontal sectional view of a part of the top portion of the CAC.
Figure 5:
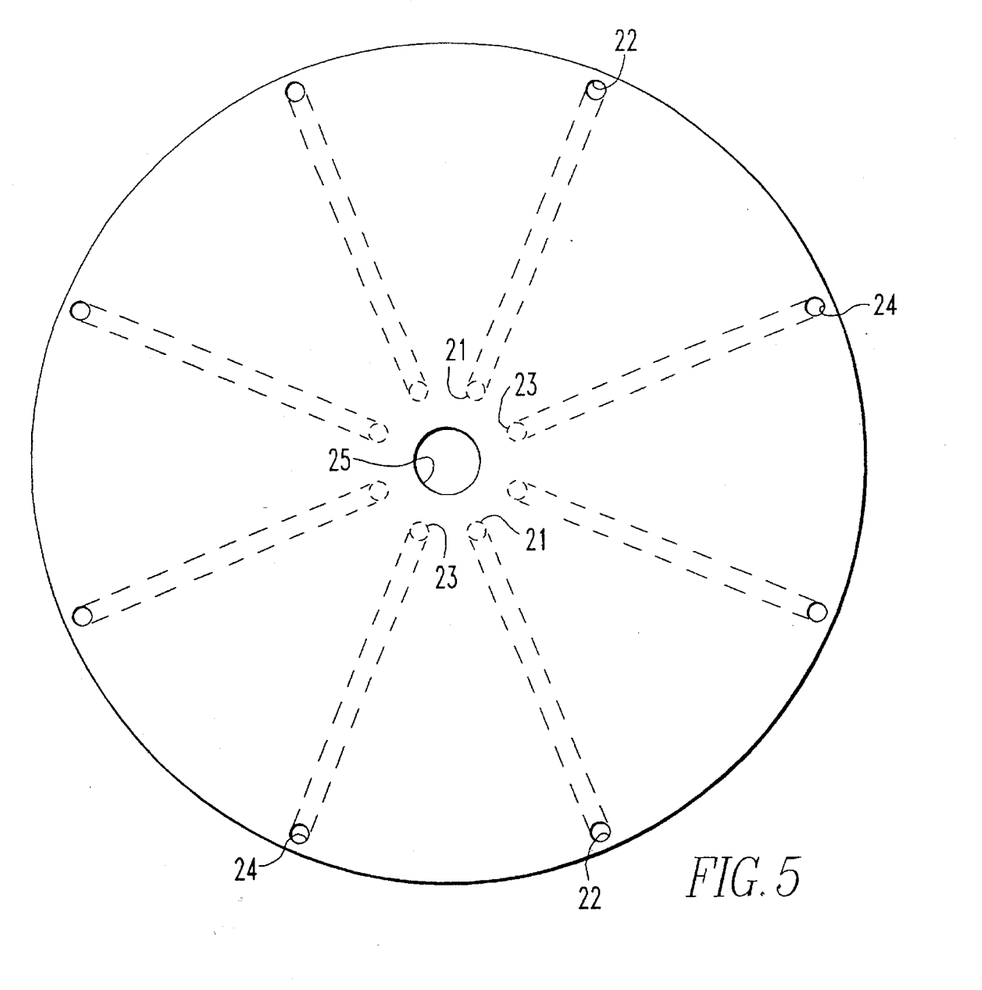
FIG. 5 is a plan view of the bottom of the embodiment shown in FIG. 4.

The central cavity defined by the inner cylinder 35 is sealed by a cap 31 so that pipe or channel 25 can be used to apply pressure to the annular bed of the resin beads 22.

Figure 6:
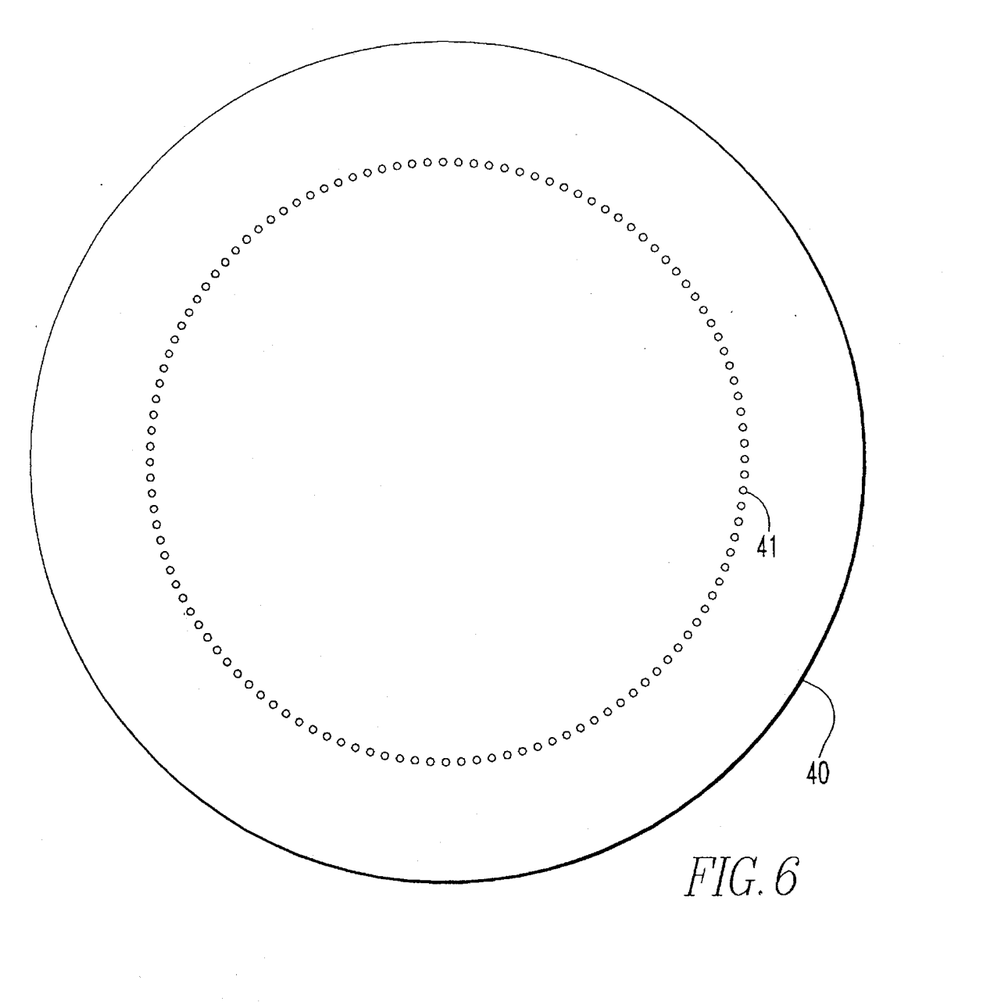
FIG. 6 is a plan view of the bottom of the CAC.

The bottom of the annular space 32 is defined by a product plate 40. As seen in FIG. 6, a large number of product delivery channels or pipes 41 pass through this plate. The allows the collection of a variety of product fractions and also facilitates adjustments to the operating conditions to allow product collection at various angular displacements.

The distributor plate 20 is held in a fixed position above the annular space 32 by a bracket 62 which is in turn connected to a support rod 61 which is affixed to a base plate 60. Also affixed to this base plate 60 is a support column 63 in which the product plate 40 rotatably rests. A shaft 70 passes through the support column 63 and base plate 60 and connects the product plate 40 to a motivating means (not shown). Also affixed to the base plate 60 is an annular collection trough 50 which can be subdivided into any number of convenient segments, each with its own exit port 51. The continuous annular chromatograph 10 is operated by rotating the annular space 32 packed with the resin beads 27 beneath the fixed distributor plate 20 and its associated feed nozzles 22 and 24. The rotational force is supplied by shaft 70. A detailed description of the CAC and its operation can be found in U.S. Pat. Nos. 5,098,678 (Lee, et al.), 5,110,566 (Snyder, et al.) and 5,174,971 (Snyder, et al.), hereby incorporated by reference herein.

The gadolinium isotopes are sequentially stripped from the ion exchange resin and form the fraction of desired isotopes as a downwardly moving band of eluant solution containing the same. The desired fraction, when it reaches the desired product port of the column, may be readily collected and separated from the remainder of the eluant solution. The isolation of the desired gadolinium isotopes is accomplished by obtaining the proper separation factor and isolating the desired gadolinium isotopes based on residence time in the proper exit port. It is preferred that the isolated solutions of the gadolinium isotopes having the high thermal neutron capture cross-sections are combined, e.g., $Gd^{155}$ $+Gd^{157}$, and then separated and/or concentrated by conventional techniques in order to recover a high thermal neutron capture cross-section enriched gadolinium compound which can be used for nuclear reactor applications.

The invention will be further clarified by a consideration of the following prophetic example, which is intended to be purely exemplary of the invention. Following the steps of the invention should result in high thermal neutron capture cross-section enriched gadolinium compounds having the beneficial properties of the invention.

EXAMPLE 1

Chromatographic separation is represented by a separation factor $\alpha$ and causes different isotopes to move through the column at rates proportional to their masses. For different separation factors, mass distributions are calculated by summing the concentrations of each isotope at various eluant volumes. (A resolution factor R is related to the separation factor and is used to develop a model of the continuous chromatographic separation of the invention.) The shape of chromatographic peaks exiting from the column (relative concentration vs. eluant volume) is represented by a gaussian peak having an area scaled in proportion to the isotope abundance.

As the separation factor is increased, the various isotope peaks become increasingly separated, and the mass distribution becomes a representation of the abundance of isotopes as the separation factor approaches 20, i.e., as the isotopes become completely separated. However, for considerably lower degree of separation, the high thermal neutron capture cross-section isotopes, e.g., $Gd^{155}$ and $Gd^{157}$, become increasingly enriched in one fraction of the elution profile, defining the high value portion of the material. Thus, well before complete separation of the isotopes is achieved, most of the value of enhancement of isotopic purification can be achieved. This model can assist in determining the desired degree of enrichment required.

Figure 7:
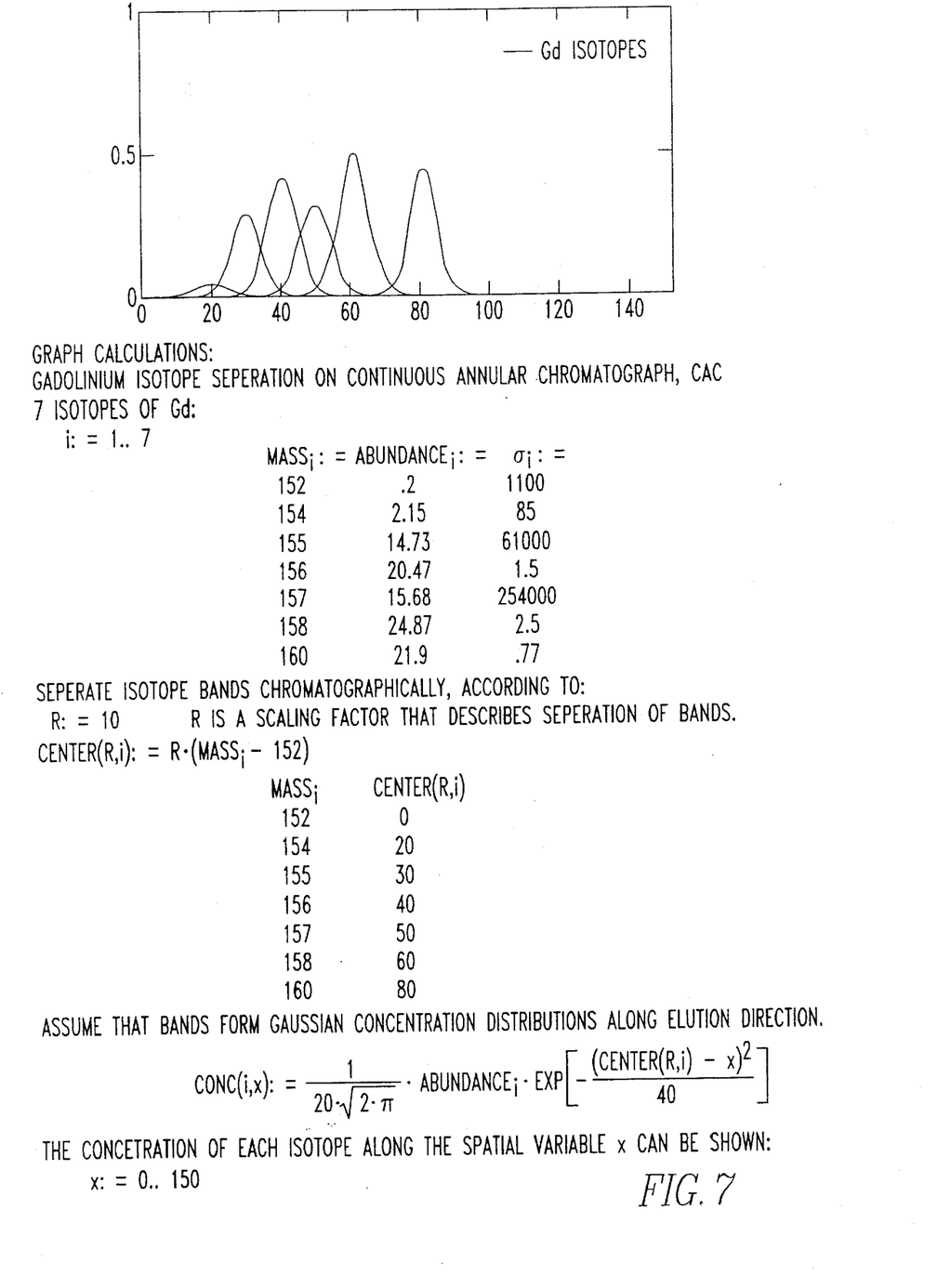
FIG. 7 is a gaussian distribution curve of isotope concentration versus elution volume showing the theoretical separation of gadolinium isotopes for a resolution factor of $R=10$.
Figure 8A:
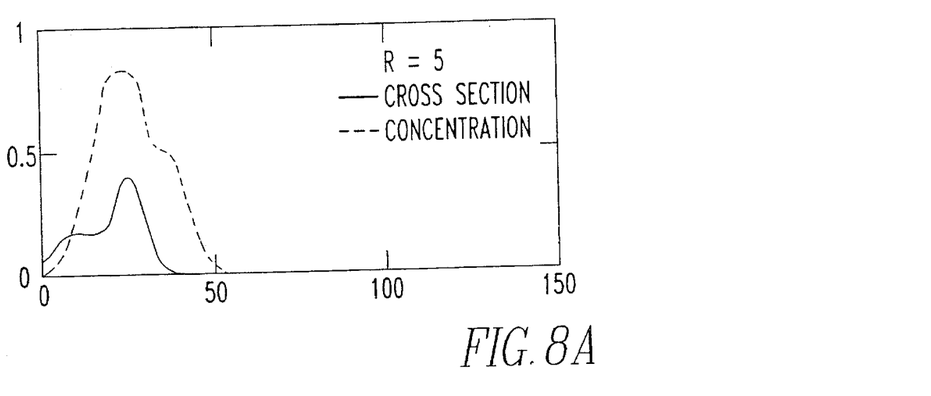
FIGS. 8A, 8B and 8C, are concentration profiles of gadolinium isotopes and neutron capture cross-section profile for resolution factors of $R=5$, 10 and 15, respectively. As the resolution factor increases, the high neutron capture cross-section isotopes become more isolated and, consequently, can be recovered by collecting the proper fraction of the output of the CAC.
Figure 8B:
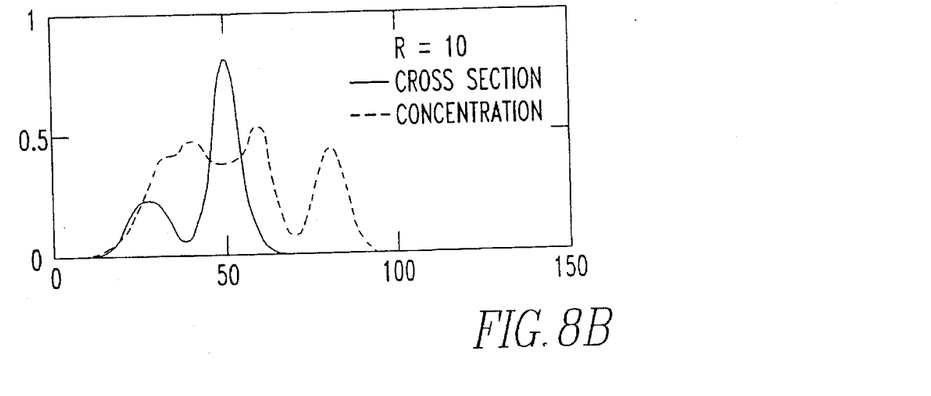
Figure 8C:
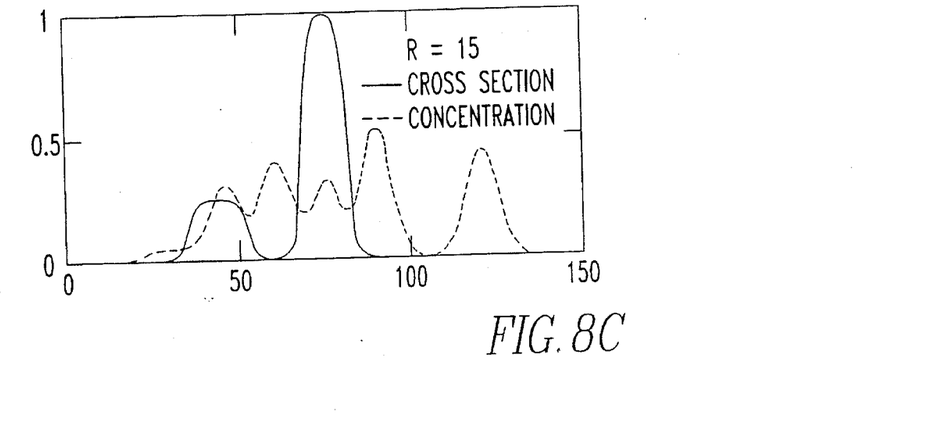

Based on this model, FIG. 7 shows a theoretical concentration profile separation of Gd isotopes and the overlap of isotope bands of Gd for a resolution factor of R=10. This is the situation where the band centers are separated by 1 band width for the isotopes separated by 1 mass unit. FIG. 8 further shows theoretical concentration profiles and thermal neutron absorption cross-section profiles for resolution factors of R=5, 10 and 15, respectively. It is clear that as the separation factor increases, the high thermal neutron absorption cross-section isotope will become isolated and consequently can be recovered by collecting the proper fraction at a distinct angular position of the CAC in a single operation.

Other embodiments of the invention will be apparent to those skilled in the art from a consideration of this specification or practice of the invention disclosed herein. It is intended that the specification and example be considered as exemplary only, with the true scope and spirit of the invention being assessed by the appended claims.

We claim:

1. A continuous, steady-state, chromatographic method for the separation of each of the isotopes of gadolinium to produce substantially pure fractions of each of the gadolinium isotopes, comprising the steps of:
   (a) subjecting a feed phase solution of gadolinium ions to continuous, steady-state, annular chromatography using a cation exchange resin as the stationary phase and an eluant solution as the mobile phase; and,
   (b) collecting simultaneously a separate isotope for each of the isotopes present in the feed phase.

2. The method of claim 1, wherein said mobile phase is an eluant acid selected from the group consisting of nitric acid, sulfuric acid, hydrochloric acid, butyric acids, phosphoric acids, oxalic acid, citric acid and acid halides.

3. The method of claim 2, wherein said mobile phase is nitric acid.

4. The method of claim 1, wherein said stationary phase comprises ion exchange resin beads having an average particle size between about 0.1–10 microns and a monodisperse particle size distribution.

5. The method of claim 4, wherein said resin beads have an exchange capacity of between 0.01 and 0.5 milliequivalent for gadolinium ions.

6. The method of claim 1, wherein the separation factor of a chromatographic column in said continuous annular chromatograph for a theoretical stage having a height of 25 cm for the separation of $Gd^{155}$ and $Gd^{157}$ is at least about 1.05.

7. A continuous, steady-state chromatographic method for the simultaneous separation of each of the isotopes of gadolinium to produce substantially pure fractions of increased thermal neutron capture cross-sections, comprising the steps of:
   (a) subjecting a feed phase solution of gadolinium ions to continuous, steady-state, chromatography using an ion exchange resin as the stationary phase and an eluant solution as the mobile phase;
   (b) collecting simultaneously at least two gadolinium product fractions, one enriched in $Gd^{155}$ isotope and the other enriched in $Gd^{157}$ isotope; and,
   (c) combining the at least two gadolinium product fractions to yield gadolinium product having increased thermal neutron capture cross-sections.

8. The method of claim 7, wherein the continuous, steady-state chromatography is effected in a continuous annular chromatograph.

9. The method of claim 8, wherein the stationary phase is a cation exchange resin.

10. The method of claim 9, wherein the mobile phase is selected from the group of acids consisting of nitric acid, sulfuric acid, hydrochloric acid, butyric acids, phosphoric acids, oxalic acid, citric acid and add halides.

11. The method of claim 10, wherein the mobile phase is nitric acid.

12. A continuous, steady-state, gadolinium isotope separation method, comprising the steps of:
   (a) loading a stationary phase into a circumferential annular space of a continuous annular chromatograph having an effective column height sufficient to resolve each of said gadolinium isotopes into a distinct product fraction having a sufficient purity, the stationary phase comprising an ion exchange resin having a monodisperse particle distribution of substantially spherical resin beads;
   (b) preparing an aqueous feed solution of gadolinium ions from a mixture of gadolinium isotopes;
   (c) preparing an eluant solution capable of displacing gadolinium ions from said ion exchange resin;
   (d) rotating said annular space of said continuous annular chromatograph;
   (e) feeding said feed solution containing gadolinium ions into the top of said annular space so that the feed solution penetrates no more than about 5% of the effective column height of the stationary phase before elution is initiated;
   (f) feeding said eluant solution into the top of said annular space to cause each of the gadolinium isotopes in said feed solution to pass down the annular space at different speeds;
   (g) collecting a separate product fraction at separate product ports at the bottom of said continuous annular chromatograph, said product fractions corresponding to each of the high thermal cross-section gadolinium isotopes present in the feed solution after elution of all of the gadolinium isotopes present in the feed solution
   (e) continuously repeating steps (e) to (g) to produce commercially useful quantities of the high thermal neutron cross-section gadolinium isotopes.

13. The method of claim 12, wherein the collecting step (g) includes at least two separate product ports for collecting at least $Gd^{155}$ and $Gd^{157}$ isotopes having high thermal neutron capture cross-sections.

14. The method of claim 13, further comprising the step of:
   (f) combining the $Gd^{155}$ and $Gd^{157}$ isotope product fractions to yield a thermal neutron capture cross-section enriched gadolinium product.

15. The method of claim 12, wherein the eluant of step (c) is nitric acid.

16. The method of claim 12, wherein the stationary phase of step (a) is a cation exchange resin.

* * * * *